(12) United States Patent
Monteith et al.

(10) Patent No.: US 8,431,536 B2
(45) Date of Patent: Apr. 30, 2013

(54) TARGET FOR BREAST CANCER THERAPY AND/OR DIAGNOSIS

(75) Inventors: Gregory Raymond Monteith, Queensland (AU); Sarah Roberts-Thomson, Queensland (AU); Damara Vanessa McAndrew, Queensland (AU)

(73) Assignee: The University of Queensland, Queensland (AU)

( * ) Notice: Subject to any disclaimer, the term of this patent is extended or adjusted under 35 U.S.C. 154(b) by 370 days.

(21) Appl. No.: 12/530,036

(22) PCT Filed: Mar. 5, 2008

(86) PCT No.: PCT/AU2008/000299
§ 371 (c)(1), (2), (4) Date: Jan. 13, 2010

(87) PCT Pub. No.: WO2008/106731
PCT Pub. Date: Sep. 12, 2008

(65) Prior Publication Data
US 2010/0119518 A1    May 13, 2010

(30) Foreign Application Priority Data

Mar. 5, 2007  (AU) ............... 2007901124

(51) Int. Cl.
*A61K 38/00*    (2006.01)
(52) U.S. Cl.
USPC ........................ 514/17.4; 514/19.4
(58) Field of Classification Search ............... None
See application file for complete search history.

(56) References Cited

U.S. PATENT DOCUMENTS

2008/0039392 A1* 2/2008 Cahalan et al. ............... 514/12

FOREIGN PATENT DOCUMENTS

| EP | 1 024 138 A1 | 8/2000 |
| WO | WO-00/40614 A2 | 7/2000 |
| WO | WO-2004/063355 A2 | 7/2004 |
| WO | WO 2004/078995 | * 9/2004 |
| WO | WO-2004/078995 A2 | 9/2004 |
| WO | WO-2006/002378 A2 | 1/2006 |
| WO | WO-2007/121186 A2 | 10/2007 |
| WO | WO-2007/139926 A2 | 12/2007 |
| WO | WO-2009/035818 A1 | 3/2009 |
| WO | WO-2009/095719 A2 | 8/2009 |

OTHER PUBLICATIONS

Peinelt et al (Nature Cell Biology, Jul. 2006, published online May 30, 2006; 8:771-773).*
Aussel et al., "Submicromolar $La^{3+}$ Concentrations Block the Calcium Release-Activated Channel, and Impair CD69 and CD 25 Expression in CD3- or Thapsigargin-Activated Jurkat Cells", *Biochemical Journal* (1996) 313:909-913.
Hiani et al., "Calcium-Sensing Receptor Stimulation Induces Nonselective Cation Channel Activation in Breast Cancer Cells", *J. Membrane Biology* (2006) 211:127-137.
Spassova et al., "STIM1 has a Plasma Membrane Role in the Activation of Store-Operated $Cat^{2+}$ Channels", *PNAS* (2006) 103:4040-4045.
Yeromin et al., "A Store-Operated Calcium Channel in Drosophila S2 Cells", *The Journal of General Physiology* (2004) 123:167-182.
Bootman et al., "2-Aminoethoxydiphenyl borate (2-APB) is a Reliable Blocker of Store-Operated $Ca^{2+}$ Entry but an Inconsistent Inhibitor of $InsP_{3-}$ induced $Ca^{2+}$ Release", *FASEB J.*, 16, 1145-1150 (2002).
Supplementary Search Report dated Aug. 5, 2010 (9 pgs.).

* cited by examiner

*Primary Examiner* — Laura B Goddard
(74) *Attorney, Agent, or Firm* — Tarolli, Sundheim, Covell & Tummino LLP

(57) ABSTRACT

The present invention relates to breast cancer and methods for identifying therapeutics and diagnosis. In general, methods for identifying therapeutic agents directed to calcium flow are disclosed. Also provided are methods for diagnosis of breast cancer and/or a predisposition to breast cancer and methods of treatment of breast cancer. The methods include identifying therapeutic agents which modulate a CRAC channel and/or a glycoprotein activator of a CRAC channel. Also provided are diagnostic methods that utilize a CRAC channel and/or a glycoprotein activator of a CRAC channel.

7 Claims, 6 Drawing Sheets

TARGET FOR BREAST CANCER THERAPY AND/OR DIAGNOSIS

FIELD OF THE INVENTION

THE present invention relates to breast cancer. In particular, the present invention relates to novel therapeutic targets and diagnostic markers for breast cancer.

BACKGROUND TO THE INVENTION

Breast cancer is one of the most common causes of cancer in women. The likelihood of developing invasive breast cancer during a woman's lifetime is approximately 1 in 7. In 2003, the global market for breast cancer was estimated at US $5 billion and is expected to rise to US $11.6 billion by 2008. For example Herceptin, a targeted therapy for women with early-stage HER2-positive breast cancer has enjoyed double-digit sales growth every year since its launch in 1998. Recently, Herceptin had a 58% spike in sales to $764 million after the release of the data for it use in early-stage breast cancer.

There is no standard treatment for breast cancer, where the current methods range from surgery and radiation, to chemotherapy, hormone therapy, and biological therapy (including, monoclonal antibody therapy) and combinations thereof. The type of treatment chosen is generally governed by the stage and type of cancer at the time of diagnosis.

Considerable commercial and academic resources are directed to identification of candidate therapeutic agents for the treatment of breast cancer. For example, Herceptin is a humanized antibody approved for the treatment of HER2-positive metastatic breast cancer. Herceptin is designed to target and block the function of HER2 protein, a growth factor protein that is overexpressed in approx 25% of breast cancer patients. A further example, Tykerb, is a dual kinase inhibitor which inhibits both ErbB-2 and EGFR kinases and may be more effective than Herceptin.

Like numerous forms of cancer, breast tumour growth is a multifactorial disease with no standardised medication available for patients. In spite of major advances in early detection and adjuvant therapy, advanced breast cancer remains a major clinical and social problem.

SUMMARY OF THE INVENTION

In a first aspect, the invention provides a method of screening, designing, engineering or otherwise producing a therapeutic agent for use in treatment of breast cancer, said method including the step of determining whether a candidate agent can (i) modulate a calcium release-activated calcium (CRAC) channel; and/or (ii) modulate a glycoprotein activator of a CRAC channel to thereby modify one or more cancer-related properties of a mammary gland cell.

In one preferred form, the candidate agent can alter a flow of calcium into a mammary gland cell.

Typically, the candidate agent can selectively modulate a CRAC channel and/or a glycoprotein activator of a CRAC channel.

Preferably, the candidate agent can selectively inhibit a CRAC channel and/or a glycoprotein activator of a CRAC channel.

In a second aspect, the invention provides a pharmaceutical composition for treating a breast cancer comprising a therapeutic agent effective for treatment of said breast cancer identified according to the first aspect, together with a pharmaceutically acceptable carrier, diluent or excipient.

In a third aspect, the invention provides a method of treating a breast cancer in a human including the step of administering to said human a therapeutic agent effective for treatment of said breast cancer screened, designed, engineered and/or otherwise produced according to the first aspect.

In particular embodiments, the CRAC channel is selected from the group consisting of CRACM1, CRACM2 and CRACM3.

Suitably, the glycoprotein activator is located on the plasma membrane of a cell.

Preferably, the glycoprotein activator is a member of the STIM family of transmembrane proteins such as STIM1 or STIM2 but is not limited thereto.

More preferably, the glycoprotein activator is STIM1.

In a fourth aspect, the invention provides a method of determining whether a human with breast cancer is potentially responsive to treatment with a therapeutic agent effective in altering a flow of calcium into a mammary gland cell, said method including the step of detecting increased expression levels of a calcium release-activated calcium (CRAC) channel and/or a glycoprotein activator in the plasma membrane of a mammary gland cell.

Preferably, said method includes measuring glycosylation levels of a glycoprotein activator in the plasma membrane of said mammary gland cell.

In a fifth aspect, the invention provides a method of determining whether a human is predisposed to breast cancer or suffering from breast cancer, said method including the step of detecting a level of a calcium release-activated calcium (CRAC) channel and/or a glycoprotein activator of a CRAC channel in a mammary gland cell.

Preferably, a level is an elevated level of the CRAC channel and/or the glycoprotein activator of a CRAC channel.

Preferably, said method includes detecting increased glycosylation levels of a glycoprotein activator in the plasma membrane of a mammary gland cell.

Preferably, the glycoprotein activator is a member of the STIM family of transmembrane proteins such as STIM1 or STIM2 but is not limited thereto.

More preferably, the glycoprotein activator is STIM1.

Throughout this specification, unless the context requires otherwise, the words "comprise", "comprises" and "comprising" will be understood to imply the inclusion of a stated integer or group of integers but not the exclusion of any other integer or group of integers.

BRIEF DESCRIPTION OF THE FIGURES

In order that the invention may be readily understood and put into practical effect, preferred embodiments will now be described by way of example with reference to the accompanying figures wherein like reference numerals refer to like parts and wherein.

DETAILED DESCRIPTION OF THE INVENTION

Figure 1:
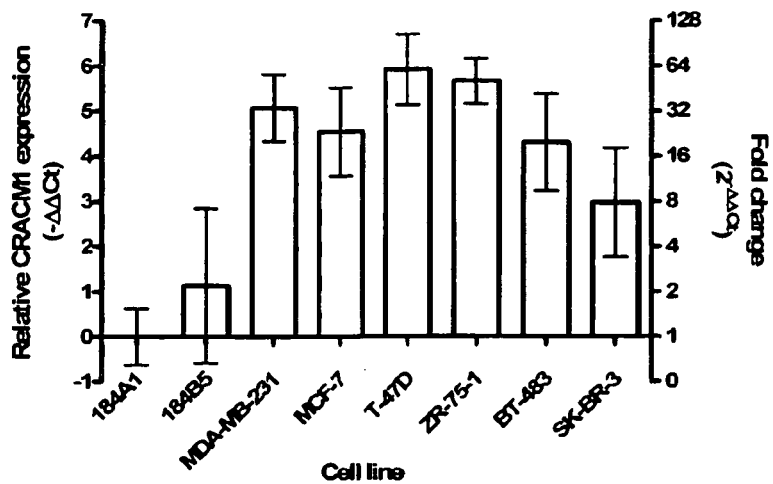
FIG. 1 Relative levels of CRACM1 expression in various breast cell lines as measured by real time RT-PCR.

Early diagnosis and treatment of breast cancer improves prognosis for a majority of patients. The present invention has identified a genuine need for novel therapeutic targets for the treatment of breast cancer to either replace or augment existing adjuvant therapy, that are specific or appropriate for breast cancer, are more physiologically relevant and which are not accompanied by the medical sequelae of cytotoxic drug exposure or surgery.

The present invention is predicated, in part, on the observation of the emerging relationship between calcium dyshomeostasis and the regulation of proliferation of breast cancer cells. The functional link between intracellular calcium levels and proliferation of breast cancer cells has been attributed by the inventors to elevated expression levels of a calcium release-activated calcium (CRAC) channel and potentially increased glycosylation of a glycoprotein activator.

Accordingly, the present invention broadly seeks to provide therapeutic and diagnostic methods for breast cancer wherein the therapeutic methods include reducing abnormally high levels of calcium in a mammary gland cell through direct modulation of calcium influx by a CRAC channel and/or modulation of a glycoprotein activator of a CRAC channel.

In particular embodiments, the CRAC channel is selected from the group consisting of CRACM1, CRACM2 and CRACM3.

By "glycoprotein activator" is meant any glycoprotein situated in the cell membrane which activates an increase in rate of calcium flow into a cell by a CRAC channel. It will be appreciated by "activate" or "activation" it is meant the capacity of a glycoprotein activator to up-regulate, stimulate, enhance or otherwise facilitate calcium flow into a cell by a CRAC channel. It is envisaged that cross-talk between the glycoprotein activator and the CRAC channel may occur by either a direct or indirect molecular interaction. Suitably, said glycoprotein activator is a transmembrane protein which is associated with, or in close proximity to, a CRAC channel.

The CRAC channels (also known in the art as Orai) are a group of calcium channels involved in capacitative calcium entry (Feske et al 2006, Nature, 441 (7090): p 179-85). CRAC channel family comprises a number of subtypes inclusive of CRACM1, CRACM2 and CRACM3 (Mercer et al 2006 J Biol Chem 281(34): 24979-90).

The STIM (where STIM is stromal interaction molecule) family of proteins is a novel class of proteins which have been implicated as the signal that couples intracellular calcium depletion to the activation of calcium influx into a cell. Presently, the STIM family consists of STIM1 and STIM2. STIM1 is known to migrate from the endoplasmic reticulum to the plasma membrane upon depletion of calcium stores (Zhang et al, 2005, Nature 437: 902-905). Furthermore, a glycosylated form of STIM1 is present on the plasma membrane.

It is known in the art that STIM1 is an essential component of CRAC channel activation. The present inventors have observed that STIM1 is expressed in numerous breast cancer cell lines. Moreover, CRACM1 and CRACM2 are excessively expressed in several breast cancer cell lines. Although not wishing to be bound by any particular theory, CRAC and STIM proteins potentially contribute to activation of proliferative pathways in breast cancer cells in the following manner (i) excessive glycosylation of a STIM in breast cancer cells results in incorrect plasma membrane accumulation of STIM and (ii) at the plasma membrane, STIM activates CRAC (by either a direct or indirect interaction), which results in excessive calcium influx into the cell and promotion of transcription, proliferation and invasiveness in breast cancer cells. Hence, CRAC/STIM pathway is an attractive target for novel therapeutics against breast cancer.

By "breast cancer" is meant a malignant tumour of the breast tissue. Throughout this specification, the term "mammary gland" will be used interchangeably with "breast".

By "mammary gland cell" is meant a cell from the mammary gland, inclusive of a non-cancerous cell, a cancerous cell, a pre-malignant cell, a neoplastic cell, a malignant cell, a tumorigenic cell, a non-tumorigenic cell and a breast cancer stem cell.

By "protein" is meant an amino acid polymer. The amino acids may be natural or non-natural amino acids, D- or L-amino acids as are well understood in the art.

The term "protein" includes and encompasses "peptide", which is typically used to describe a protein having no more than fifty (50) amino acids and "polypeptide", which is typically used to describe a protein having more than fifty (50) amino acids.

By "glycoprotein" is meant a protein comprising a carbohydrate moiety (e.g. an oligosaccharide or polysaccharide).

In light of the foregoing, in one broad aspect the invention provides a method of designing, screening and/or engineering therapeutic agents for treating breast cancer wherein a candidate agent inhibits plasma membrane calcium transportation pathways.

In preferred embodiments, the invention relates to a method of designing, screening and/or engineering therapeutic agents for treating breast cancer by determining whether a candidate agent can modulate all or part of the CRAC/STIM pathway in a mammary gland cell which, in turn, modifies one or more cancer-related properties of the mammary gland cell.

By "cancer-related properties" is meant any physiological and/or pathological manifestation of a cell which results from cancer of the cell. Within the scope is promotion of transcription, proliferation of the cell, death of the cell (such as apoptosis and necrosis) and invasiveness, wherein invasiveness is inclusive of metastasis, migration and loss of adhesion.

It will be appreciated that in general forms, a candidate agent may directly modulate a CRAC channel.

In an alternative form, a candidate agent may modulate a glycoprotein activator of a CRAC channel to thereby alter calcium flow into a mammary gland cell.

In the context of the present invention, "alter" or "alteration" includes within its scope a decrease, lowering or otherwise down-regulation of calcium flow across a plasma membrane. It is envisaged that alteration of calcium flow into a mammary gland cell includes selective alteration of calcium flow.

It will be readily appreciated that the mechanism of "modulation", "modulator" or "modulating" includes within its scope any interaction which interferes with, inhibits, blocks or hinders or activates or augments either the calcium-flow related activity of the CRAC channel and/or a glycoprotein activator of a CRAC channel. In certain embodiments, the modulator is an inhibitor. In other embodiments, the modulator is an antagonist. In yet other embodiments, the modulator is an agonist. In further embodiments, the modulator is an activator.

In a particularly preferred embodiments of the present invention, the candidate agent selectively modulates a CRAC channel and/or a glycoprotein activator of a CRAC channel.

In other particularly preferred embodiments of the present invention, the candidate agent selectively inhibits a CRAC channel and/or a glycoprotein activator of a CRAC channel.

By "selective" or "selectively" is meant a candidate agent that primarily affects a CRAC channel and/or a glycoprotein activator of a CRAC channel but may also have an effect upon other channels, and in particular, other calcium channels. Therefore in one embodiment, "selective" or "selectively" encompasses a situation where at least 50%, 55%, 60%, 65%, preferably at least 70%, 75%, 80%, 85% and more preferably 90%, 95%, 96%, 98%, 99% and 100% of the calcium flow activity of a candidate agent can be attributable to a CRAC channel and/or a glycoprotein activator of a CRAC channel.

In another embodiment, "selective" or "selectively" includes a candidate agent that can bind to and inhibit a CRAC channel and/or a glycoprotein activator of a CRAC channel. A non-limiting example of such a candidate agent is a suitable binding and/or interaction partner, such as a protein. In particular embodiments, the protein is an antibody.

In yet another embodiment, "selective" or "selectively" includes a candidate agent that specifically regulates a CRAC channel and/or a glycoprotein activator of a CRAC channel such as, but not limited to, nucleic acid molecules.

In yet a further embodiment, "selective" or "selectively" includes a candidate agent that specifically regulates post-translational forms of a CRAC channel and/or a glycoprotein activator of a CRAC channel.

In a preferred embodiment, the candidate agent alters calcium flow by inhibition of a CRAC channel and/or a glycoprotein activator of a CRAC channel.

Accordingly, modulators may be peptides, proteins such as antibodies or other organic molecules, preferably small organic molecules, with a desired biological activity and half-life.

It is envisaged that both polyclonal and monoclonal antibodies directed to either the entire protein or a biologically-active fragment thereof are suitable modulators.

By "biologically-active fragment" is meant a fragment, portion, region or segment of a protein which displays at least 10%, preferably at least 25%, more preferably at least 50% and even more preferably at least 70%, 80% or 90% of the biological activity of the entire or full-length protein.

In relation to a CRAC channel, biological activity is calcium transport activity.

With regard to a glycoprotein activator, the biological activity is the ability to activate calcium transport into a cell by either a direct or indirect interaction with a CRAC channel.

It will be appreciated by a person of skill in the art that antibodies employed for therapeutic applications in humans must have specific properties which make these antibodies suitable for use in humans. Generally, therapeutic antibodies are "humanised", wherein the antibody typically comprises over 90% human sequence and the complementary determining regions of murine antibodies. Humanised antibodies are particularly advantageous for medical applications due to the decrease likelihood of eliciting a foreign body immune reaction.

In one particular embodiment, the modulating agent is a humanised antibody directed to a glycosylated form of STIM.

In an alternative embodiment, said modulator is an antibody directed to a phosphorylated form of STIM.

It in envisaged that humanised antibodies may be directed to any STIM such as, but not limited to, STIM1 and STIM2. Preferably, the humanised antibody is directed to STIM1.

In other particular embodiments, the modulating agent is an antibody directed to a CRAC channel. In an alternative particular embodiment, the antibody directed to a CRAC channel is directed to CRACM1.

It is readily contemplated that effective modulating agents include other potential CRAC channel inhibitors which may be useful according to the present invention such as, but not limited to, SKF-96365, T182, YM-58483, BTP-2 and lanthanides such as, but not limited to, gadolinium.

In a particularly preferred embodiment, the modulating agent is a selective modulator of a CRAC channel such as $La^{3+}$ and 2-aminoethoxydiphenyl borate, but is not limited thereto. WO 07/081804 and WO 07/121186 provide non-limiting examples of suitable CRAC-specific modulating agents and are incorporated herein by reference.

It is further contemplated that a molecular biological approach to modulation of the CRAC/STIM pathway may be employed. RNA interference, and in particular (but not limited thereto) siRNA, provides an attractive method for silencing of potential therapeutic gene targets by sequence-specific cleavage of cognate mRNA. Takeshita and Ochiya (Cancer Sci, 2006, 97: 689-696) provides numerous examples of the therapeutic potential of RNA interference against cancer and is incorporated herein by reference.

The term "gene" is used herein to describe a discrete nucleic acid locus, unit or region within a genome that may comprise one or more of introns, exons, splice sites, open reading frames and 5' and/or 3' non-coding regulatory sequences such as a promoter and/or a polyadenylation sequence.

Therefore a person of skill in the art will readily appreciate that the invention contemplates a genetic construct which comprises one or more nucleotide sequences capable of directing synthesis of an RNA molecule, said nucleotide sequence selected from the list comprising: —

(i) a nucleotide sequence transcribable to an RNA molecule comprising an RNA sequence which is substantially homologous to an RNA sequence encoded by a nucleotide sequence of interest;

(ii) a reverse complement of the nucleotide sequence of (i);

(iii) a combination of the nucleotide sequences of (i) and (ii), (iv) multiple copies of nucleotide sequences of (i), (ii) or (iii), optionally separated by a spacer sequence;

(v) a combination of the nucleotide sequences of (i) and (ii), wherein the nucleotide sequence of (ii) represents an inverted repeat of the nucleotide sequence of (i), separated by a spacer sequence; and (vi) a combination as described in (v), wherein the spacer sequence comprises an intron sequence spliceable from said combination;

Where the nucleotide sequence comprises an inverted repeat separated by a non-intron spacer sequence, upon transcription, the presence of the non-intron spacer sequence facilitates the formation of a stem-loop structure by virtue of the binding of the inverted repeat sequences to each other. The presence of the non-intron spacer sequence causes the transcribed RNA sequence (also referred to herein as a "transcript") so formed to remain substantially in one piece, in a form that may be referred to herein as a "hairpin". Alternatively, where the nucleotide sequence comprises an inverted repeat wherein the spacer sequence comprises an intron sequence, upon transcription, the presence of intron/exon splice junction sequences on either side of the intron sequence facilitates the removal of what would otherwise form into a loop structure. The resulting transcript comprises a double-stranded RNA (dsRNA) molecule, optionally with overhanging 3' sequences at one or both ends. Such a dsRNA transcript is referred to herein as a "perfect hairpin". The RNA molecules may comprise a single hairpin or multiple hairpins including "bulges" of single-stranded DNA occurring in regions of double-stranded DNA sequences.

Depending upon the application, the RNA molecule may directed to a single target or alternatively, a plurality of targets.

In particular embodiments, the RNA molecule encodes CRACM1, CRACM2 or CRACM3 and/or STIM1 or STIM2.

Non-limiting examples of suitable siRNA molecules, and in particular CRAC-specific siRNA, according to the present invention include the following duplexes of sense RNA (first nucleotide sequence) and antisense RNA (second nucleotide sequence):

```
                                          (SEQ ID NO: 1)
(i)    GGCCUGAUCUUUAUCGUCUUU;

(SEQ ID NO: 2)
       AGACGAUAAAGAUCAGGCCUU;

(SEQ ID NO: 3)
(ii)   GCACCUGUUUGCGCUCAUGUU;

(SEQ ID NO: 4)
       CAUGAGCGCAAACAGGUGCUU;

(SEQ ID NO: 5)
(iii)  UCAACGAGCACYCCAUGCAUU;

(SEQ ID NO: 6)
       UGCAUGGAGUGCUCGUUGAUU;
```

Persons skilled in the art will be aware that anti-breast cancer therapeutic agents of the invention may be identified by any number of methods. Accordingly, designing, screening, engineering and/or producing methods involves determination of whether a candidate agent can directly modulate a CRAC channel and/or modulation of a glycoprotein activator of a CRAC channel. In preferred embodiments, methods of the invention involve determining whether the candidate agent can alter a flow of calcium into a breast cell by modulating a CRAC channel and/or modulation of a glycoprotein activator of a CRAC channel.

In one embodiment, anti-breast cancer therapeutic agents may be identified by way of screening libraries of molecules such as synthetic chemical libraries, including combinatorial libraries, by methods such as described in Nestler & Liu, 1998, Comb. Chem. High Throughput Screen. 1 113 and Kirkpatrick et al., 1999, Comb. Chem. High Throughput Screen 2 211.

It is also contemplated that libraries of naturally-occurring molecules may be screened by methodology such as reviewed in Kolb, 1998, Prog. Drug. Res. 51 185.

More rational approaches to designing anti-breast cancer agents may employ X-ray crystallography, NMR spectroscopy, computer assisted screening of structural databases, computer-assisted modelling, or more traditional biophysical techniques which detect molecular binding interactions, as are well known in the art.

A review of structural bioinformatics approaches to drug discovery is provided in Fauman et al, 2003, Meth. Biochem. Anal. 44: 477.

Computer-assisted structural database searching and bioinformatic approaches are becoming increasingly utilized as a procedure for identifying and/or engineering agonists and antagonist molecules. Examples of database searching methods may be found in U.S. Pat. No. 5,752,019 and International Publication WO 97/41526 (directed to identifying EPO mimetics) and U.S. Pat. Nos. 7,158,891 and 5,680,331 which are directed to more general computational approaches to protein modelling and structural mimicry of protein activity.

Generally, other applicable methods include any of a variety of biophysical techniques which identify molecular interactions. Methods applicable to potentially useful techniques such as competitive radioligand binding assays, electrophysiology, analytical ultracentrifugation, microcalorimetry, surface plasmon resonance and optical biosensor-based methods are provided in Chapter 20 of CURRENT PROTOCOLS IN PROTEIN SCIENCE Eds. Coligan et al., (John Wiley & Sons, 1997) which is incorporated herein by reference.

A person skilled in the art will appreciate that modulating agents may be in the form of a binding partner and as such, identified by interaction assays such as yeast two-hybrid approaches and the like, but without limitation thereto. Two-hybrid screening methods are provided in Chapter 20 of CURRENT PROTOCOLS IN PROTEIN SCIENCE Eds. Coligan et al., (John Wiley & Sons, 1997) which is incorporated herein by reference.

It is also contemplated that in one aspect, the invention provides a pharmaceutical composition comprising a therapeutic agent effective for treatment of breast cancer screened, designed, engineered and/or otherwise produced as hereinbefore described, together with a pharmaceutically-acceptable carrier, diluent or excipient.

In another aspect, the invention provides a method of treating breast cancer in a human including the step of administering to said human a therapeutic agent effective for treatment of breast cancer designed, screened, engineered and/or otherwise produced as hereinbefore described.

Preferably, the therapeutic agent effective for treatment of breast cancer is in the form of a small organic molecule, peptide or the like formulated with a pharmaceutically-acceptable carrier, diluent or excipient suitable for oral administration, as a transdermal patch or other non-invasive route of administration.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991) which is incorporated herein by reference.

Any safe route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular and transdermal administration may be employed.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Pharmaceutical compositions of the present invention suitable for oral or parenteral administration may be presented as discrete units such as capsules, sachets or tablets each containing a pre-determined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more agents as described above with the carrier which constitutes one or more necessary ingredients. In general, the compositions are prepared by uniformly and intimately admixing the agents of the invention with liquid carriers or finely divided solid carriers or both, and then, if necessary, shaping the product into the desired presentation.

The above compositions may be administered in a manner compatible with the dosage formulation, and in such amount as is pharmaceutically-effective. The dose administered to a patient, in the context of the present invention, should be sufficient to effect a beneficial response in a patient over an appropriate period of time. The quantity of agent(s) to be administered may depend on the subject to be treated inclusive of the age, sex, weight and general health condition thereof, factors that will depend on the judgement of the practitioner.

Broadly, the invention is directed towards diagnostic methods for breast cancer which utilise CRAC channels and glycoprotein activators as diagnostic markers.

The present invention provides a new and advantageous method for diagnosis of breast cancers that are associated with lactation. The most pertinent example of such a breast cancer is pregnancy-associated breast cancer. Approximately 3% of breast cancers are associated with pregnancy. Because metastasis is common, pregnancy-associated breast cancer has a higher mortality rate than other cancers. Moreover, the risk of pregnancy-associated breast cancer is higher in older first time mothers. Hence as the average child-bearing age increases, the incidence of pregnancy-associated breast cancer and its higher mortality rate will also rise, which underscores the importance of effective and timely diagnosis for this form of breast cancer.

In one general aspect, the invention provides a diagnostic method for determining if a patient is likely to respond to treatment with a therapeutic agent for a sub-set of breast cancer associated with lactation.

In one particular aspect, the invention provides a diagnostic method for determining whether a patient may be responsive to treatment with a therapeutic agent that alters calcium influx via CRAC/STIM pathway by measuring glycosylation levels of plasma membrane associated STIM in a mammary gland cell.

In one particular embodiment, the invention provides a diagnostic method for determining if a human is predisposed to or is suffering from breast cancer by detecting whether plasma membrane associated STIM is excessively glycosylated in a mammary gland cell.

In another particular aspect, the diagnostic methods of the present invention includes measurement of the ratio of one particular form of STIM relative to another particular form of STIM.

In an alternative or additional embodiment, the invention provides a diagnostic method to detect activation of CRAC channel expression. It is envisaged that CRAC channel expression may be analysed by either protein-based or nucleic acid-based techniques.

Thus "predisposed" and "predisposition" are used in the context of a probability that an individual may display clinical symptoms of breast cancer, or that any existing, manifest clinical symptoms of breast cancer are the result of an underlying biochemical cause.

It will be readily appreciated by a person of skill in the art that a number of methods may be utilised to measure the expression levels of STIM on the plasma membrane of a mammary gland cell. By way of example only, fluorescence activated cell sorting (FACS) analysis using labelled antibodies is readily amenable to quantitative measurement of cell surface expression of proteins. For example, immunofluorescence and other fluorescence microscopy methods can also be used to stain breast tissue to detect levels of glycosylated STIM as well as other conventional immunohistochemistry techniques.

Alternatively, relative protein expression levels may be determined by other protein-based methods which include immunoassays, for example ELISA and immunoblotting to detect relative expression levels of one or more of said proteins.

The invention further contemplates use of microarray technology to determine the expression pattern profile of mammary gland cells in order to analyse whether glycosylated STIM expression or CRAC channel expression is up-regulated in patients with breast cancer.

Proteomic pattern analysis provides an alternative diagnostic method which is particularly useful for global expression pattern analysis of proteins. Methods of cancer diagnosis using proteomic patterns are provided in Conrads et al Expert Rev Mol Diagn. 2003 July; 3(4):411-20 and is incorporated herein by reference.

In particular embodiments, a plurality of said proteins may be used in a protein library displayed in a number of ways, e.g., in phage display or cell display systems or by two-dimensional gel electrophoresis, or more specifically, differential two-dimensional gel electrophoresis (2D-DIGE). These particular embodiments may generally be referred to as "proteomic" or "protein profiling" methods, such as described in Chapters 3.9.1 and 22 of CURRENT PROTOCOLS IN PROTEIN SCIENCE Eds. Coligan et al., John Wiley & Sons NY USA (1996-2002).

In embodiments relating to protein arrays, preferably a breast cancer-associated protein of the invention is located at an identifiable address on the array.

Preferably, the protein array comprises a substrate to which is immobilized, impregnated, bound or otherwise coupled breast cancer-associated protein, or a fragment thereof.

The substrate may be a chemically-derivatized aluminium chip, a synthetic membrane such as PVDF or nitrocellulose, a glass slide or microtiter plates.

Detection of substrate-bound proteins may be performed using mass spectrometry, ELISA, immunohistochemistry, fluorescence microscopy or by colorimetric detection.

A person of skill in the art will the diagnostic methods of the invention may involve measuring expression levels of a nucleic acid encoding a STIM and/or a CRAC channel. In this regard, nucleotide sequence variations in a promoter, for example, may affect the steady state levels of a CRAC channel gene transcript in one or more cells of an affected or predisposed individual.

It is also contemplated that relative levels of nucleic acids may be measured and/or compared in the diagnostic methods of the present invention. By way of example, a CRAC and STIM mRNA levels may be measured.

Measurement of relative levels of a nucleic acid level compared to an expressed level of a reference nucleic acid may be conveniently performed using a nucleic acid array.

Nucleic acid array technology has become well known in the art and examples of methods applicable to array technology are provided in Chapter 22 of CURRENT PROTOCOLS IN MOLECULAR BIOLOGY Eds. Ausubel et al. (John Wiley & Sons NY USA 1995-2001).

An array can be generated by various methods, e.g., by photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

Reference is also made to Affymetrix nucleic acid array systems such as described in U.S. Pat. No. 5,858,659 and U.S. Pat. No. 6,300,063 which provide specific teaching in relation to nucleic acid array-based detection of disease-related polymorphisms.

In another particular form of this embodiment, quantitative or semi-quantitative PCR using primers corresponding to CRAC channel-encoding nucleic acids or STIM-encoding nucleic acids may be used to quantify relative expression levels of a CRAC channel nucleic acid or STIM nucleic acid to thereby determine whether an individual is predisposed to or suffering from breast cancer.

PCR amplification is not linear and hence end point analysis does not always allow for the accurate determination of nucleic acid expression levels.

Real-time PCR analysis provides a high throughput means of measuring gene expression levels. It uses specific primers, and fluorescence detection to measure the amount of product after each cycle. Hydridization probes utilise either quencher dyes or fluorescence directly to generate a signal. This method may be used to validate and quantify nucleic acidexpression differences in cells or tissues obtained from breast cancer sufferers compared to cells or tissues obtained from non-sufferers.

So that the invention may be readily understood and put into practical effect, the following non-limiting Examples are provided.

EXAMPLES

Example 1

Expression of CRACM1, CRACM2 and STIM1 in Breast Cancer Cell Lines

Figure 2:
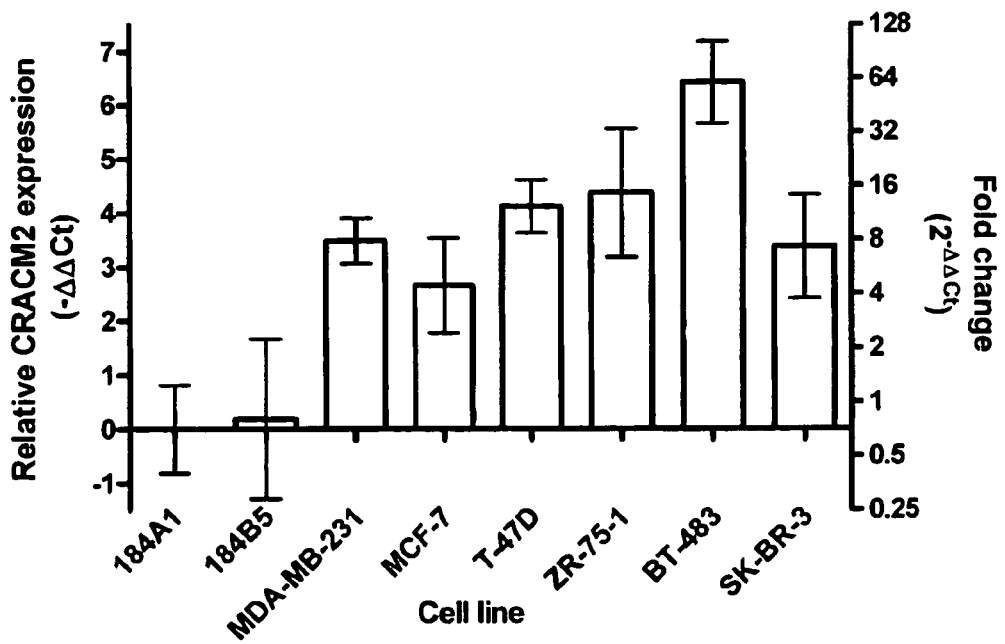
FIG. 2 Relative levels of CRACM2 expression in various breast cell lines as measured by real time RT-PCR.
Figure 3:
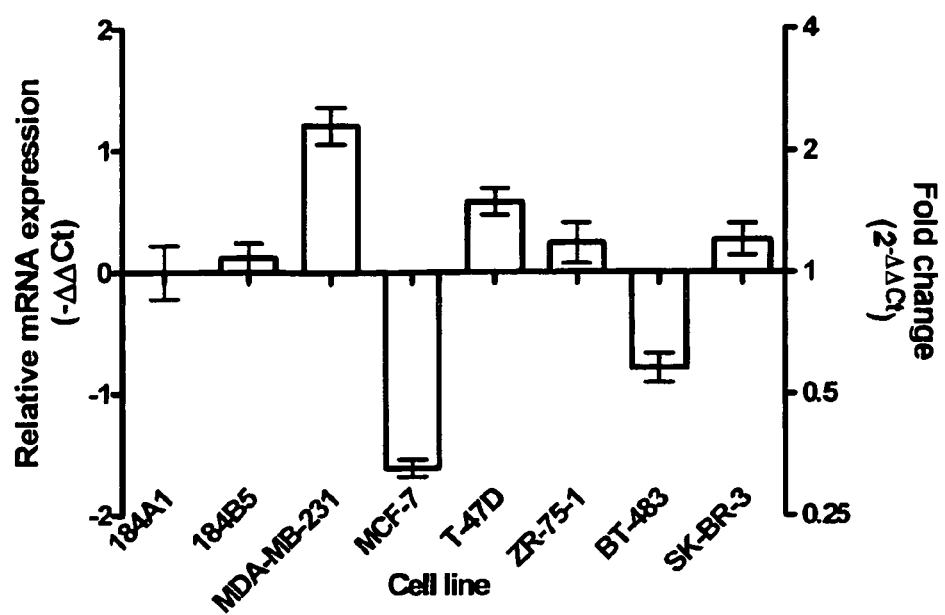
FIG. 3 Relative levels of STIM1 expression in various breast cell lines as measured by real time RT-PCR.

Real time RT-PCR using Taqman® assays have shown that CRACM1 and CRACM2 is expressed in the breast cancer cell lines MCF-7, MDA-MB-231, T47D, ZR-75-1, BT-483, SK-BR3 and all breast cancer cell lines have greater levels of CRACM1 and CRACM2 than the normal breast cell lines (184A1, 184B5). Result of this analysis are depicted in FIG. 1 and FIG. 2 respectively. FIG. 3 shows that STIM1 expression is increased in MDA-MB-231, T47D, BT-483, SK-BR3 breast cancer cell lines relative to normal breast cell lines.

Example 2

Effect of Blocking CRACM1 on Proliferation/Viability of Breast Cancer Cells

Figure 5:
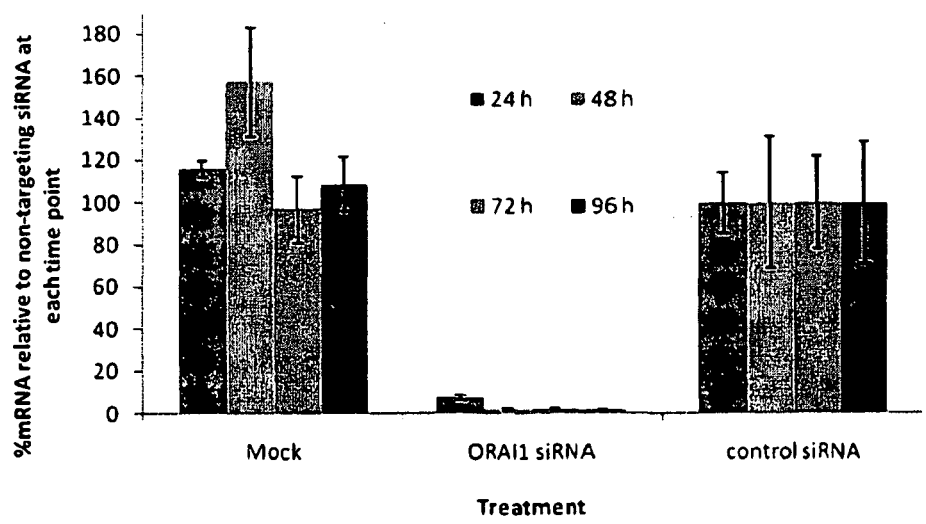
FIG. 5 Knockdown of CRACM1 mRNA in MCF-7 breast cancer cells using CRACM1 (orai1) siRNA.
Figure 6:
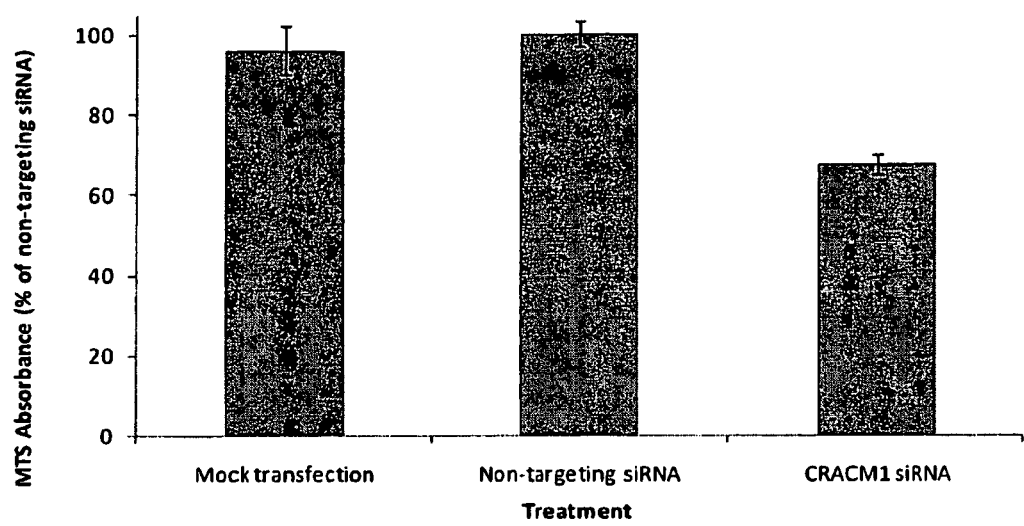
FIG. 6 The effect of siRNA to CRACM1 (96 hrs) on the viability of MCF-7 cells, as measured by an MTS assay for cellular proliferation. Normalized MTS absorbance (proliferation/viability) of the mean of 3 independent experiments in MCF-7 breast cancer cells (±SEM). For each experiment absorbance was assessed in quadruplicate. Experiment was performed in 1% foetal bovine serum (p<0.05).
Figure 8:
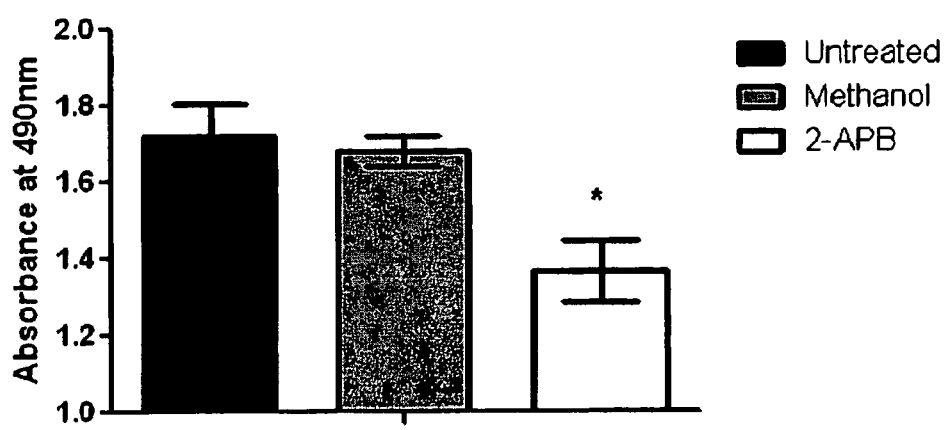
FIG. 8 MTS assay of MCF-7 cells treated with 50 μM 2-APB. * p<0.05 compared with respective methanol control. Error bars=SD. Cells were treated with 2-APB on plating in 10% foetal bovine serum. MTS assay was performed 72 hrs after plating.

Reduction of CRACM1 (ORAI-1) mRNA levels by CRACM1 siRNA (Dharmacon) was confirmed by real time RT-PCR in MCF-7 breast cancer cells (FIG. 5). CRACM1 siRNA inhibited the viability/proliferation of MCF-7 breast cancer cells compared to controls as assessed by an MTS proliferation assay (FIG. 6). The CRAC inhibitor 2-APB inhibits the proliferation/viability of MCF-7 breast as assessed by an MTS proliferation assay (FIG. 8).

Example 3

Figure 4A:
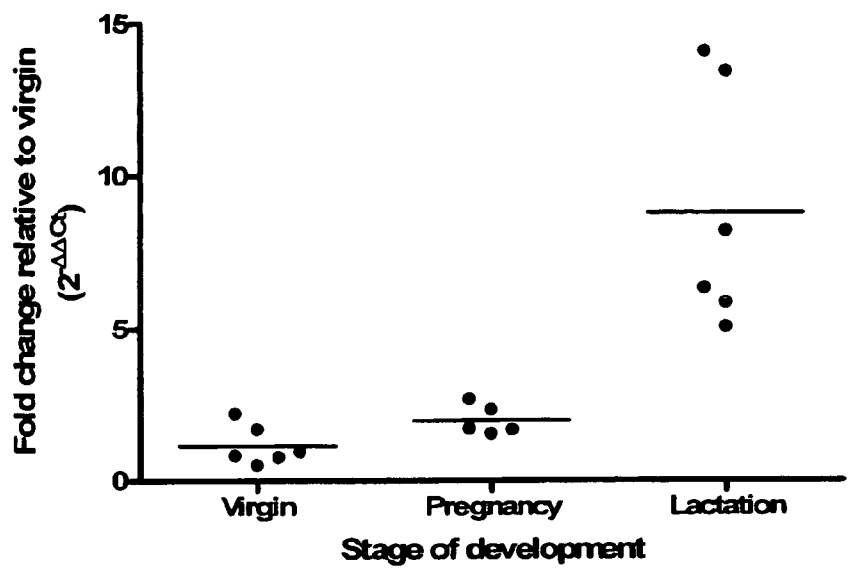
FIG. 4 The relative levels of CRACM1 (FIG. 4A), STIM1 (FIG. 4B) and STIM2 (FIG. 4C) in a mouse mammary gland as assessed by real time RT-PCR.
Figure 4B:
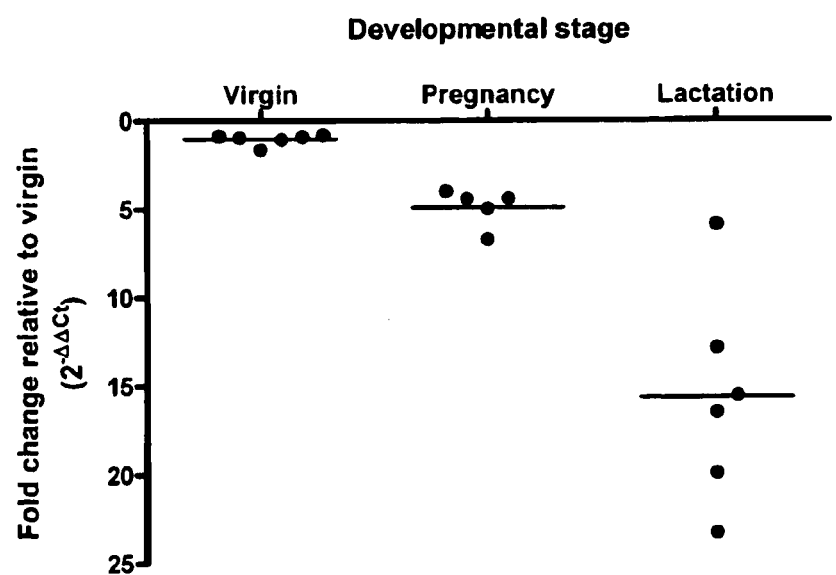
Figure 4C:
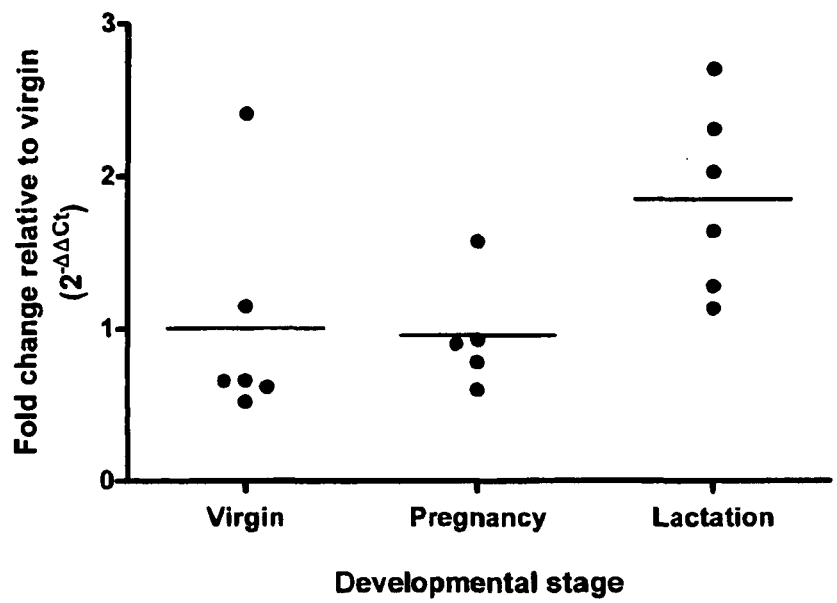
Figure 7:
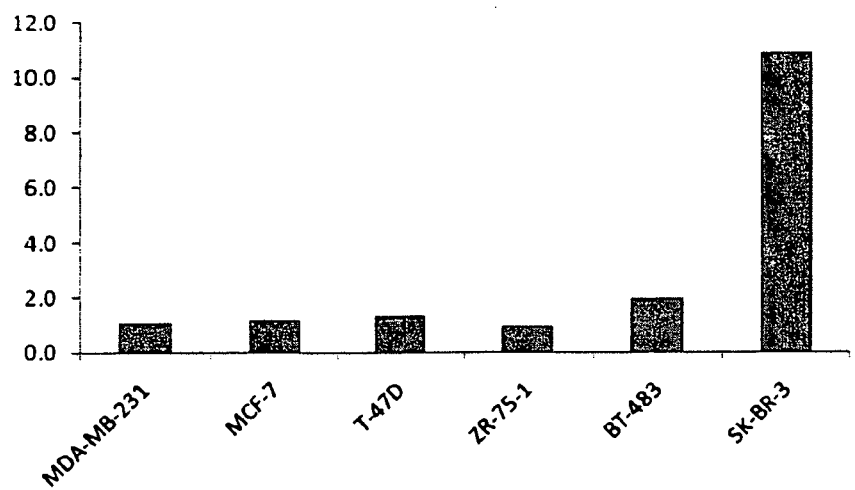
FIG. 7 Comparison of the relative STIM1/STIM2 ratio in various breast cancer cell lines. Relative STIM1 and STIM2 mRNA levels was assessed using real time RT-PCR and the relative ratio calculated.

Alterations in CRACM1 and STIM1 mRNA are a feature of mammary gland development and the STIM1/STIM2 ratio is altered in some breast cancer cell lines. During lactation CRACM1 levels increase and STIM1 levels decline relative to mammary glands from virgin (nulliparous) mice as assessed by real time RT-PCR (FIG. 4). The STIM1 and STIM2 ratio is altered in the SK-BR-3 breast cancer cell line compared with other breast cancer cell lines assessed by real time RT-PCR (FIG. 7).

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

The invention claimed is:

1. A method of treating a breast cancer in which a CRAC channel level and/or a glycoprotein activator of a CRAC channel level are elevated in a mammary gland cell in a human, said method including the step of administering to said human a therapeutic agent effective for treatment of said breast cancer, wherein said therapeutic agent selectively inhibits a CRAC channel and selectively inhibits a glycoprotein activator of a CRAC channel in a mammary gland cell or selectively inhibits a CRAC channel in a mammary gland cell to thereby modify one or more cancer-related properties of a mammary gland cell.

2. The method of treating breast cancer in a human according to claim 1, wherein the CRAC channel is selected from the group consisting of CRACM1, CRACM2 and CRACM3.

3. The method of treating breast cancer in a human according to claim 2, wherein the CRAC channel is CRACM1.

4. The method of treating a breast cancer in a human according to claim 1, wherein the glycoprotein activator of a CRAC channel is a STIM protein.

5. The method of treating a breast cancer in a human according to claim 4, wherein the STIM protein is selected from the group consisting of STIM1 and STIM2.

6. The method of treating a breast cancer in a human according to claim 5, wherein the STIM protein is STIM1.

7. The method of treating a breast cancer in a human according to claim 1, wherein said therapeutic agent is selected from the group consisting of $La^{3+}$ and 2-APB.

* * * * *

SEQUENCE LISTING

<160> NUMBER OF SEQ ID NOS: 6

<210> SEQ ID NO 1
<211> LENGTH: 21
<212> TYPE: RNA
<213> ORGANISM: Homo sapiens

<400> SEQUENCE: 1
ggccugaucu uuaucgucuu u                                             21

<210> SEQ ID NO 2
<211> LENGTH: 21
<212> TYPE: RNA
<213> ORGANISM: Homo sapiens

<400> SEQUENCE: 2
agacgauaaa gaucaggccu u                                             21

<210> SEQ ID NO 3
<211> LENGTH: 21
<212> TYPE: RNA
<213> ORGANISM: Homo sapiens

<400> SEQUENCE: 3
gcaccuguuu gcgcucaugu u                                             21

<210> SEQ ID NO 4
<211> LENGTH: 21
<212> TYPE: RNA
<213> ORGANISM: Homo sapiens

<400> SEQUENCE: 4
caugagcgca aacaggugcu u                                             21

<210> SEQ ID NO 5
<211> LENGTH: 21
<212> TYPE: RNA
<213> ORGANISM: Homo sapiens

<400> SEQUENCE: 5
ucaacgagca cyccaugcau u                                             21

<210> SEQ ID NO 6
<211> LENGTH: 21
<212> TYPE: RNA
<213> ORGANISM: Homo sapiens

<400> SEQUENCE: 6
ugcauggagu gcucguugau u                                             21